US012691442B2

(12) United States Patent
Liu et al.

(10) Patent No.: US 12,691,442 B2
(45) Date of Patent: Jul. 28, 2026

(54) SUPPORTED METAL CATALYST WITH SYNERGISTIC SITES, A PREPARATION METHOD THEREFOR AND AN APPLICATION THEREOF

(71) Applicant: Beijing University of Chemical Technology, Beijing (CN)

(72) Inventors: Yanan Liu, Beijing (CN); Dianqing Li, Beijing (CN); He Yu, Beijing (CN); Ning Li, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 500 days.

(21) Appl. No.: 18/452,032

(22) Filed: Aug. 18, 2023

(65) Prior Publication Data

US 2024/0082833 A1     Mar. 14, 2024

(30) Foreign Application Priority Data

Sep. 13, 2022     (CN) ........................... 202211110171.0
Mar. 21, 2023     (CN) ........................... 202310282510.1

(51) Int. Cl.
| | |
|---|---|
| *B01J 37/02* | (2006.01) |
| *B01J 21/04* | (2006.01) |
| *B01J 27/045* | (2006.01) |
| *B01J 27/051* | (2006.01) |
| *B01J 35/30* | (2024.01) |
| *B01J 35/61* | (2024.01) |
| *B01J 35/63* | (2024.01) |
| *B01J 35/64* | (2024.01) |
| *B01J 37/04* | (2006.01) |
| *B01J 37/06* | (2006.01) |
| *B01J 37/08* | (2006.01) |
| *B01J 37/16* | (2006.01) |
| *C07C 1/30* | (2006.01) |
| *C07C 5/32* | (2006.01) |
| *C07C 29/145* | (2006.01) |

(52) U.S. Cl.
CPC ........... *B01J 37/0201* (2013.01); *B01J 21/04* (2013.01); *B01J 27/045* (2013.01); *B01J 27/051* (2013.01); *B01J 27/0515* (2013.01); *B01J 35/394* (2024.01); *B01J 35/613* (2024.01); *B01J 35/615* (2024.01); *B01J 35/633* (2024.01); *B01J 35/635* (2024.01); *B01J 35/638* (2024.01); *B01J 35/647* (2024.01); *B01J 37/0236* (2013.01); *B01J 37/04* (2013.01); *B01J 37/06* (2013.01); *B01J 37/08* (2013.01); *B01J 37/16* (2013.01); *C07C 1/30* (2013.01); *C07C 5/322* (2013.01); *C07C 29/145* (2013.01); *C07C 2521/02* (2013.01); *C07C 2523/28* (2013.01); *C07C 2523/72* (2013.01); *C07C 2527/051* (2013.01)

(58) Field of Classification Search
CPC ......... B01J 21/04; B01J 27/045; B01J 27/051
See application file for complete search history.

(56) References Cited

PUBLICATIONS

M. Vrinat, et al., 317, Journal of alloys and compounds 195-200 (2001)("Vrinat") (Year: 2001).*
M. Taniguchi, et al., 187.1 Journal of Catalysis 139-150 (1999)("Taniguchi") (Year: 1999).*
P. W. Dimmock, et al., , J. Chem. Soc. Dalton Trans. 955 (1991)("Dimmock") (Year: 1991).*

* cited by examiner

*Primary Examiner* — Alexander R Pagano
*Assistant Examiner* — Frank S. Hou

(57)     ABSTRACT

The present invention provides a preparation method of a supported metal catalyst with synergistic sites. The method is to utilize the unsaturated cubane-like structure, M cation with catalytic activity is introduced into the cluster core unit. By using the vertex vacancy as the capturing center, and adjusting the impregnation temperature to maximize the loading of the cluster precursor, Depending on the electrostatic adsorption of the support and the confinement of the cluster structural unit, the number of S vacancies and the distance between S vacancies and Miso sites are effectively controlled through liquid phase reduction and atmosphere treatment at room temperature to obtain supported X3MSx/Al2O3 catalyst with Miso-Vs synergistic sites. The method of the present invention achieves the joint enhancement of the activity, product selectivity, and stability of unsaturated carbon oxygen bond selective hydrogenation, carbon chlorine bond selective hydrogenation dechlorination, and carbon hydrogen bond dehydrogenation reactions.

4 Claims, 4 Drawing Sheets

SUPPORTED METAL CATALYST WITH SYNERGISTIC SITES, A PREPARATION METHOD THEREFOR AND AN APPLICATION THEREOF

TECHNICAL FIELD

The present invention belongs to the fields of petrochemical engineering, fine chemical engineering and environmental chemical engineering, and relates in particular to a supported metal catalyst with synergistic sites and a preparation method therefor. The catalyst is mainly used in selective hydrogenation of C=O bond, hydrodechlorination of C—Cl bond and dehydrogenation of C—H bond.

BACKGROUND ART

Global targets of sustainable development in the energy and environmental fields have seen site-isolated catalysts receive widespread attention due to their maximal atom utilization and special catalytic behavior, which is associated with low coordination number, quantum confinement of metal atoms, and/or strong interactions with the catalyst support. Traditional fabrication strategies for site-isolated catalysts have been developed, which are highly dependent upon the initial adsorption/binding of a metal precursor with a support and the introduction of second metal as well as often require lower metal loading to be effective.

For instance, Zhang et al. explored the impact of different particle sizes in $Pt/Al_2O_3$ catalysts on the activity and selectivity of propane dehydrogenation (PDH) reaction in Size Dependence of Pt Catalysts for Propane Dehydrogenation: from Atomically Dispersed to Nanoparticles, *ACS Catal.* 2020, 10, 21, 12932-12942. It was found that the activity of propane dehydrogenation increased with the decrease of Pt particle size, while the selectivity showed a volcanic curve. When Pt particles dispersed at atomic level, $Pt_1/Al_2O_3$ catalyst showed the most preferred selectivity, but its activity (<25%) still needed to be further improved. To solve this problem, researchers found that the introduction of a second component can not only highly disperse the active metals, but also modify the electronic structure, and thus enhance simultaneously the catalytic activity and selectivity. In the literature Construction of a Unique Structure of Ru Sites in the RuP Structure for Propane Dehydrogenation, *ACS Appl. Mater. Interfaces* 2021, 13, 28, 33045-33055, Yang et al. introduced a proper amount of P into Ru-based catalysts to form Ru-based phosphide catalysts. Compared with monometallic Ru-based catalysts, strong electron interaction was produced between P and Ru, which can further improve the adsorption capacity of reactants while maintaining high selectivity, thus enhancing the catalytic activity. In the literature Fabrication of Supported Pd—Ir/Al₂O₃ Bimetallic Catalysts for 2-ethylanthraquinone Hydrogenation. AIChE J. 2017, 63, 3955, Hong et al. further optimized the bimetallic structure, and obtained a series of Pd—Ir catalysts with alloy structure. It was found that the ordering degree of alloy had a significant influence on the selective hydrogenation performance of anthraquinone. The experimental results showed that the alloy construction not only reduced the particle size of Pd active component, but also effectively reduced the energy barrier of anthraquinone hydrogenation. More importantly, the Pd—Ir alloy catalyst with higher ordering degree reduced the continuous Pd sites due to more significant geometric effect, which was conducive to prevent the hydrogenation of benzene ring in anthraquinone molecules to generate over-hydrogenation products, and thus improved the selectivity to a certain extent. However, challenges still emerge from the heterogeneity of such a system (namely, the metal atoms can locate at different support sites). Also, owing to high surface free energy, individual metal atoms are generally mobile on the support surface and thus aggregate, especially in reaction processes occurring at elevated temperatures. As a consequence of these points, the development of alternative fabrication strategies to prepare well-defined and stable site-isolated catalysts with higher metal loading are very desirable, albeit challenging.

Trinuclear transition metal-sulfur cluster compound $[X_3S_4L_a]^{n+}$ has attracted extensive attention due to its unsaturated cubane-like structure, stable X—S bond, outstanding stability, relatively independent structures as well as weak agglomeration effect. More importantly, the vertex vacancies in cluster core ions can serve as the capture center to anchor the metal ions (Pd, Pt, Ni, Cu, Ga, etc.) with valence electron number less than 10 to form a complete cubane-like structure, which provides a new platform for the preparation of site-isolated supported metal catalysts.

The present invention utilizes the structural characteristic of unsaturated cubane-like clusters to introduce metal M cations with hydrogenation activity into cluster units to prepare heteronuclear M-based atomic clusters, forming precursors with effectively isolated potential active sites. Then, large-pore $Al_2O_3$ is used as the support to coordinately load by the temperature-controlled impregnation strategy, and further the treating atmosphere is utilized to induce the formation of sulfur vacancies and promot the change of electronic structure of active M species, and thus construct a highly dispersed supported $X_3MS_x/Al_2O_3$ catalyst with $M_{iso}$-$V_s$ synergistic sites to improve the activity, selectivity and stability of selective hydrogenation, dehydrogenation and dechlorination catalysts.

SUMMARY OF THE INVENTION

The purpose of the present invention is to provide a supported metal catalyst with synergistic sites, a preparation method therefor and an application thereof. The supported catalyst disclosed by the present invention is expressed as $MX_3S_x/Al_2O_3$, wherein x represents sulfur-containing number in the range of 0<x<4; $MX_3S_x$ is an active component, with M as an active metal being one of Pd, Pt, Co, Ni, Ru, Ga, Fe, Cu and Ag; X represents a transition metal being one of Mo, W, Re and Ir; $Al_2O_3$ is a support; and the corresponding loading of M is 0.03~5.00 wt. %; The structure of the catalyst is characterized in that the $MX_3S_x$ (0<x<4) active component is stably dispersed on the $Al_2O_3$ support, in which $M_{iso}$ presents a geometric site isolation, and forms a $M_{iso}$-$V_s$ synergistic sites with the adjacent S vacancies.

Taking trinuclear transition metal-sulfur cluster as a precursor, M with hydrogenation activity is introduced into the precursor cluster core unit. By adopting temperature-controlled impregnation method to load the active component on $Al_2O_3$, a series of $MX_3S_x/Al_2O_3$ catalysts with $M_{iso}$-$V_s$ synergistic sites are obtained after liquid phase reduction and atmosphere treatment. The controllable construction of discontinuous M sites is realized based on the cluster structure confinement effect and charge redistribution. While maintaining the advantages of the above geometric structure, the electron structure of metallic $M_{iso}$ species can be modified by inducing the generation of S vacancies ($V_s$) through atmosphere treatment, and thus obtain the $M_{iso}$-$V_s$ synergistic sites with controllable electronic structure and type. This catalyst possesses high conversion and selectivity of target product in selective hydrogenation/dehydrogenation/dechlorination reaction, which is easy to recycle and reuse, and exhibits good stability.

A preparation method of the corresponding supported metal catalyst with synergistic sites disclosed by the present invention comprises the following specific steps:

A. Mix a soluble metal M salt solution uniformly with a cluster compound $[X_3S_4(H_2O)_y]Cl_z$ solution, wherein the molar ratio of M to $X_3$ is 4~25/1, and the concentration of the M salt is 0.0035-0.0171 mol/L;

The corresponding soluble metal M salt is one of $Na_2PdCl_4$, $Pd(NO_3)_2$, $Pd(C_5H_7O_2)_2$, $H_2PtCl_6$, $Pt(NO_3)_2$, $CoCl_2$, $Ni(NO_3)_2 \cdot 6H_2O$, $NiCl_2$, $RuCl_3$, $Ga(NO_3)_3$, $Fe(NO_3)_3 \cdot 9H_2O$, $CuCl_2 \cdot 2H_2O$, $Cu(NO_3)_2$ and $AgNO_3$.

The corresponding $[X_3S_4(H_2O)_y]Cl_z$ is a trinuclear transition metal cluster with an unsaturated cubane structure, wherein X is one of Mo, W, Re and Ir; y=9; when X is $Re^{(+3)}$, z=1; when X is one of W, Mo and $Ir^{(+4)}$, z=4.

B. Disperse $Al_2O_3$ support uniformly into the mixed solution in step A, stir at the temperature of 25~60° C. and the rotation speed of 200~500 rpm for 2~6 h until it becomes sticky, and dry it in a constant temperature drying oven at 40~80° C. for 8~24 h to obtain $[X_3MS_4(H_2O)_{y+1}]^{z+}/Al_2O_3$ solid powder;

The corresponding $Al_2O_3$ support possesses rich pore structure while the crystalline phase is $\gamma$ or $\delta$, the specific surface area is 70~190 $m^2$/g, the pore volume is 0.3~1.3 $cm^3$/g, and the pore size is 15~30 nm; the theoretical loading of the soluble metal M salt is 0.03~5.00 wt. %, preferably 0.05~2.50 wt. %;

C. Add 1.5 g of the solid powder obtained in step B into 5~30 mL of deionized water, add excessive soluble reducing agent to reduce $M^{2+}/M^{3+}$ to M metal, wherein the molar ratio of the reducing agent to the M salt is 3:1~7:1, stir for 18~60 min to obtain black suspension, centrifugally wash it to neutrality, and dry it in a constant temperature drying oven at 60° C. for 8~16 h to obtain $X_3MS_4/Al_2O_3$;

The corresponding soluble reducing agent is one of $NaBH_4$, $LiBH_4$, ascorbic acid and oxalic acid;

D. Place the $X_3MS_4/Al_2O_3$ obtained in step C into an atmosphere furnace, and heat it to 300~600° C. at a rate of 5~20° C./min for 0.25~6 h of treatment to obtain $X_3MS_x/Al_2O_3$ catalyst (0<x<4);

The corresponding treatment atmosphere is one of air, 10 vol. % $O_2/N_2$, 5~40 vol. % $H_2/N_2$ or 5~40 vol. % $CO/N_2$; and the corresponding $X_3MS_x/Al_2O_3$ catalyst possesses $M_{iso}$-$V_s$ synergistic sites.

A $[X_3S_4(H_2O)_y]Cl_z$ cluster solution is prepared by dissolving thiometalate in deionized water to prepare a solution with a concentration of 50~120 mmol/L, alternately dropping excessive reducing agent and acid solution, and fully stirring at room temperature to obtain a suspension, crystallizing it at 60~100° C. for 10~20 h, adding acid solution dropwise to keep pH value of the suspension in the range of 1~3 during the crystallization process, and making it naturally cool down to room temperature after the color of the suspension turns dark green to obtain a $[X_3S_4(H_2O)_y]Cl_z$ cluster solution;

The corresponding thiometalate is one of $(NH_4)_2MoS_4$, $(NH_4)_2WS_4$, $Na_2[Mo_2O_2S_2(cys)_2] \cdot 4H_2O$, $[PPh_4]2[ReS(S_2C_2$—$(SiMe_3)_2)(\mu$-$S)_2ReS(S_2C_2$—$(SiMe_3)_2)]$ and $[CpIr(SH)(\mu_2$-$SH)_2IrCp\ (SH)]$;

The corresponding soluble reducing agent is one of $NaBH_4$, $LiBH_4$, ascorbic acid and oxalic acid;

The corresponding acid solution is one of 6 mol/L HCl solution, 2 mol/L HCl solution and perchloric acid solution.

The preparation method is characterized in that by utilizing the unsaturated cubane-like structure of the trinuclear transition metal-sulfur cluster, M cation with catalytic activity is introduced into the cluster core unit. By using the vertex vacancy as the capturing center, and adjusting the impregnation temperature to maximize the loading of the cluster precursor, as well as depending on the electrostatic adsorption of the support and the confinement of the cluster structural unit, the number of S vacancies and the distance between S vacancies and $M_{iso}$ sites are effectively controlled through liquid phase reduction and atmosphere treatment at room temperature to obtain supported $X_3MS_x/Al_2O_3$ catalyst with $M_{iso}$-$V_s$ synergistic sites. The preparation method solves the problem that active metal particles with small particle sizes prepared by traditional methods are easy to agglomerate, which guarantees high hydrogenation activity, product selectivity and excellent stability. The preparation method features simple process without the need of adding surfactant. The catalyst is mainly used in selective hydrogenation and dechlorination in important fine chemical processes as well as propane dehydrogenation reaction in petrochemical industry, showing excellent activity and target product selectivity.

FIG. 1 shows X-Ray Diffraction (XRD) results of the $Pd^{\delta+}Mo_3S_3/Al_2O_3$ catalyst prepared in Embodiment 1, from which it can be seen that the prepared catalyst has an outstanding crystalline structure.

FIG. 2 shows CO-IR spectra of the $Pd^{\delta+}Mo_3S_3/Al_2O_3$ catalyst prepared in Embodiment 1. It can be seen that the linear adsorption peak of CO on palladium species appears above 2100 $cm^{-1}$, but there is no obvious CO bridging-adsorbed peak on $Pd^0$, which indicates that the active Pd components in the catalyst exhibits no obvious agglomeration, while continuous Pd sites are effectively isolated.

FIG. 3 shows XPS spectra of the $Pd^{\delta+}Mo_3S_3/Al_2O_3$ catalyst and $Pd/Al_2O_3$ catalyst prepared in Embodiment 1, where A is the Pd 3d XPS spectra of the $Pd^{\delta+}Mo_3S_3/Al_2O_3$ catalyst and $Pd/Al_2O_3$ catalyst, while B is the S 2p XPS spectrum of the $Pd^{\delta+}Mo_3S_3/Al_2O_3$ catalyst. It can be seen that the Pd site is electron-deficient, forming $Pd^{\delta+}$ species. Compared with $Pd/Al_2O_3$ catalyst, the electron cloud density of Pd species in $Pd^{\delta+}Mo_3S_3/Al_2O_3$ catalyst is reduced by using molybdenum-sulfur cluster as a precursor. After atmosphere treatment, there is no obvious signal of S species on the surface of the catalyst, indicating that the formation of S vacancy ($V_s$).

FIG. 4 shows the ESR spectra of the $Pd^{\delta+}Mo_3S_3/Al_2O_3$ catalyst and pure $Al_2O_3$ prepared in Embodiment 1. It can be seen that an obvious S vacancy (g=2.003) is formed, which is related to the results in FIG. 3, indicating the existence of $Pd^{\delta+}$—$V_s$ synergistic sites.

FIG. 5 shows the curve of hydrogenation efficiency versus time for the $Pd^{\delta+}Mo_3S_x/Al_2O_3$ catalyst prepared in Embodiment 1 in the selective hydrogenation of anthraquinone. When the reaction time is 120 min, the hydrogenation efficiency reaches 15.7 g/L.

FIG. 6 shows the reusability of $Pd^{\delta+}Mo_3S_3/Al_2O_3$ catalyst prepared in Embodiment 1 in selective hydrogenation reaction of anthraquinone. After the catalyst is reused for five times, the hydrogenation efficiency remains at 11.2 g/L and the target product selectivity is 96%±2%.

FIG. 7 shows the catalytic results of the $PtMo_3S_3/Al_2O_3$ catalyst prepared in Embodiment 2 in propane dehydrogenation, where A is the curve of propane conversion versus time, and B is the curve of propylene selectivity versus time. When the reaction temperature is 580° C., the initial conversion is 68% and the propylene selectivity is 90%.

FIG. 8 shows the catalytic results of $NiMo_3S_{2.1}/Al_2O_3$ catalyst prepared in Embodiment 3 in the hydrodechlorination of dichloroethane, where A is the histogram of conversion and selectivity, and B is the reusability curve. When the reaction temperature is 300° C., the initial conversion is 85% and the olefin selectivity is 96%.

THE BENEFICIAL EFFECTS OF THE INVENTION

Based on the structural characteristics of trinuclear transition metal-sulfur cluster, a novel $MX_3S_x/Al_2O_3$ (0<x<4) catalyst with $M_{iso}$-$V_s$ synergistic sites is obtained by utilizing the unsaturated cubane-like structure of the trinuclear transition metal-sulfur cluster, M cation with catalytic activity is introduced into the cluster core unit. By using the vertex vacancy as the capturing center, and adjusting the impregnation temperature to maximize the loading of the cluster precursor, as well as depending on the electrostatic adsorption of the support and the confinement of the cluster structural unit. The preparation method features simple process without the need of adding surfactant.

The prepared active metal components are uniformly dispersed on the surface of the support, which realizes the effective isolation of continuous M sites. By effectively controlling the number of S vacancies and the distance between S vacancies and $M_{iso}$ sites, $X_3MS_x/Al_2O_3$ catalyst with $M_{iso}$-$V_s$ sites with enhanced synergistic effect is obtained. The catalyst can be applied to selective hydrogenation of C=O bond, hydrodechlorination of C—Cl bond and dehydrogenation of C—H bond, and exhibits excellent activity and selectivity, easy recovery and reuse, and good stability on the premise of reducing the amount of precious metals.

DETAILED DESCRIPTION OF EMBODIMENTS

Embodiment 1

Figures 1, 2:
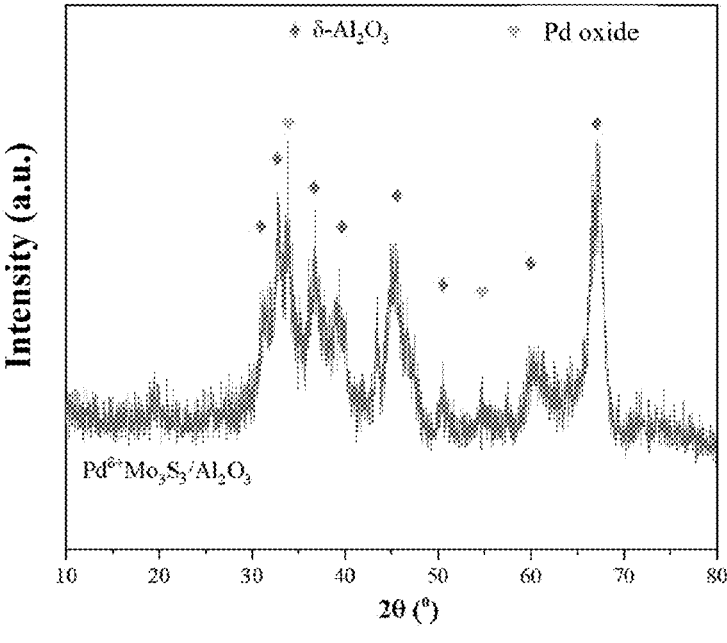
FIG. 1 shows XRD results of the $Pd^{\delta+}Mo_3S_3/Al_2O_3$ catalyst prepared in Embodiment 1.
FIG. 2 shows CO-IR spectra of the $Pd^{\delta+}Mo_3S_3/Al_2O_3$ catalyst prepared in Embodiment 1.
Figure 3:
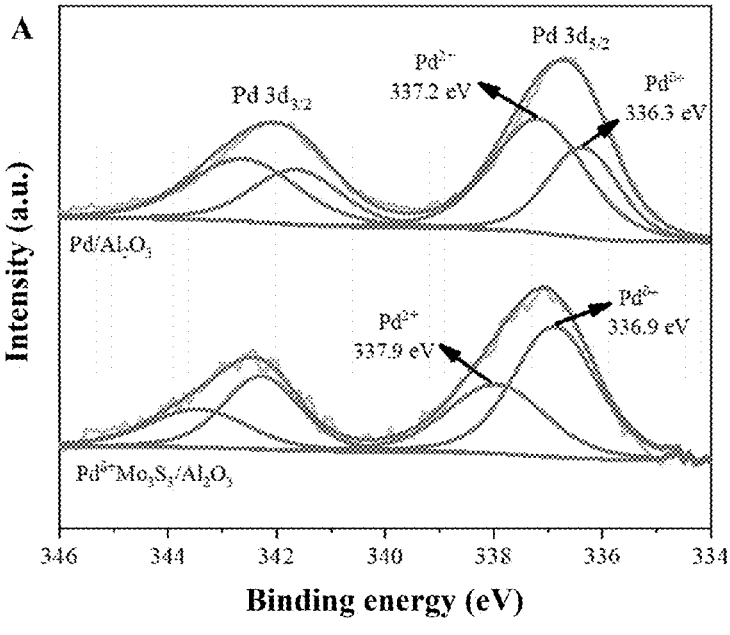
FIG. 3 shows the XPS spectra of the $Pd^{\delta+}Mo_3S_3/Al_2O_3$ catalyst and $Pd/Al_2O_3$ catalyst prepared in Embodiment 1, where A is the Pd 3d XPS spectra of the $Pd^{\delta+}Mo_3S_3/Al_2O_3$ catalyst and $Pd/Al_2O_3$ catalyst, while B is the S 2p XPS spectrum of the $Pd^{\delta+}Mo_3S_3/Al_2O_3$ catalyst.
Figure 3:
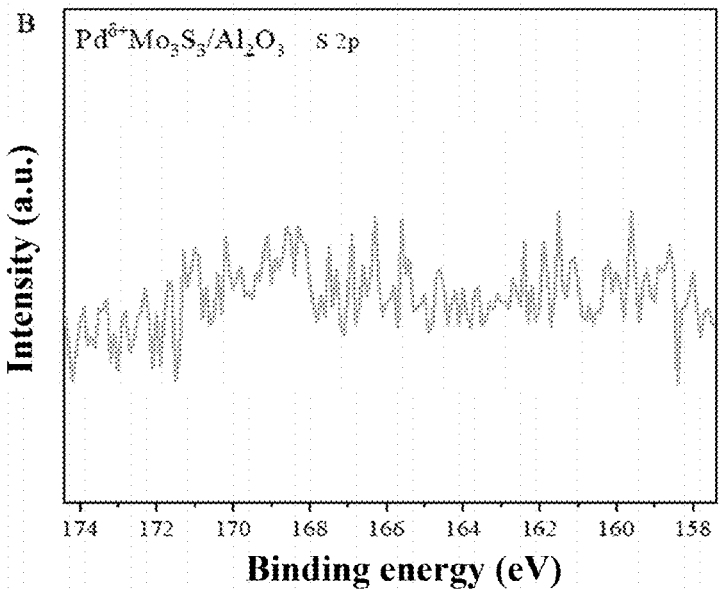
Figure 4:
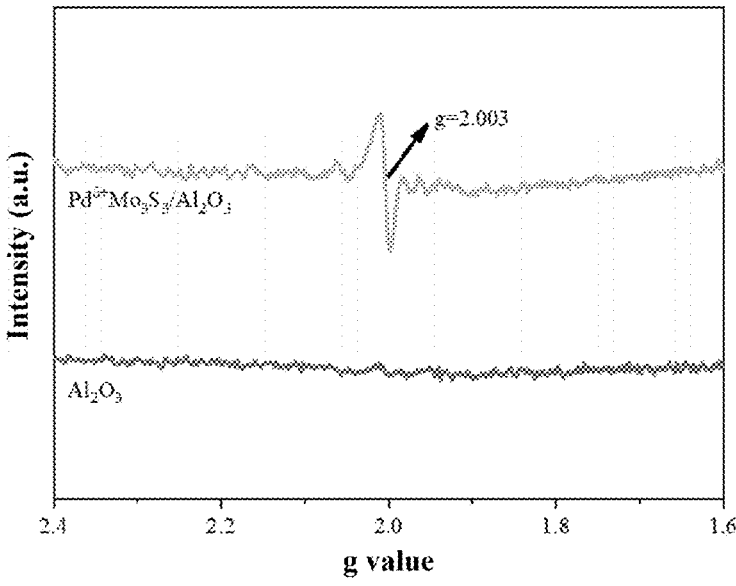
FIG. 4 shows the ESR spectra of the $Pd^{\delta+}Mo_3S_3/Al_2O_3$ catalyst and pure $Al_2O_3$ prepared in Embodiment 1.

A. Stir and mix 5.64 mL soluble metallic $Na_2PdCl_4$ solution with a concentration of 50 mmol/L and 5 mL $[Mo_3S_4(H_2O)_9]Cl_4$ solution with a concentration of 12.8 mmol/L to obtain a solution containing heteronuclear Pd-based $[Mo_3PdS_4(H_2O)_{10}]Cl_4$ atomic cluster;

B. Calcine pseudo-boehmite at 960° C. to obtain $Al_2O_3$ support with rich pore structure. According to the theoretical loading of the metallic M being 0.4 wt. %, disperse 1.5 g $Al_2O_3$ support uniformly into 10.64 mL mixed solution obtained in step A, continuously stir at 60° C. and 300 rpm for 4 h until it becomes sticky, and dry it in a constant temperature drying oven at 60° C. for 12 h to obtain $[Mo_3PdS_4(H_2O)_{10}]Cl_4/Al_2O_3$ solid powder;

C. Add 1.5 g solid powder obtained in step B into 10 mL deionized water, add 0.0533 g $NaBH_4$ as a reducing agent, stir for 30 minutes, centrifuge and wash the obtained black suspension to neutral while washing away soluble sodium salts, and dry at 60° C. in a constant temperature drying oven for 12 h to obtain $Mo_3PdS_4/Al_2O_3$;

D. Place the $Mo_3PdS_4/Al_2O_3$ obtained in step C into an atmosphere furnace, heat it to 450° C. at the rate of 10° C./min in air and calcine it for 4 h to obtain the $Mo_3PdS_x/Al_2O_3$ catalyst; and the corresponding $Mo_3PdS_x/Al_2O_3$ catalyst (x=3) has $Pd_{iso}$—$V_s$ synergistic sites.

It can be seen from Table 1 that the catalyst has rich pore structure and large specific surface area.

TABLE 1

| Test results of specific surface area and pore size of $Al_2O_3$ and $PdMo_3S_3/Al_2O_3$ | | | |
|---|---|---|---|
| Sample | Specific Surface Area $(m^2/g)$ | Specific Pore Volume $(cm^3/g)$ | Pore Size (nm) |
| $Al_2O_3$ | 87 | 0.37 | 16.69 |
| $Pd^{\delta+}Mo_3S_3/Al_2O_3$ | 86 | 0.34 | 15.55 |

The corresponding prepared catalyst is used in the selective hydrogenation experiment of anthraquinone:

Weigh 25 mg of the corresponding catalyst and 60 mL 2-ethylanthraquinone working solution (120 g/L) and put them into a 100 mL reactor. Introduce hydrogen to 0.3 MPa, heat it to 50° C., and then turn on stirring (at a speed of 1,000 rpm), and periodically open the liquid valve to take 1 mL working solution for analysis. See the results in FIG. 5 and FIG. 6.

Figure 5:
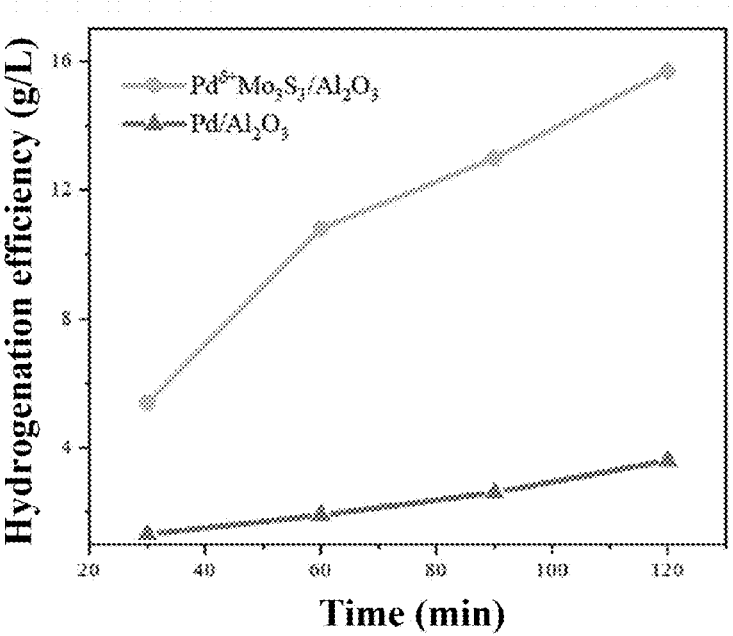
FIG. 5 shows the curve of hydrogenation efficiency versus time of the $Pd^{\delta+}Mo_3S_3/Al_2O_3$ catalyst prepared in Embodiment 1 in the selective hydrogenation of anthraquinone.
Figure 6:
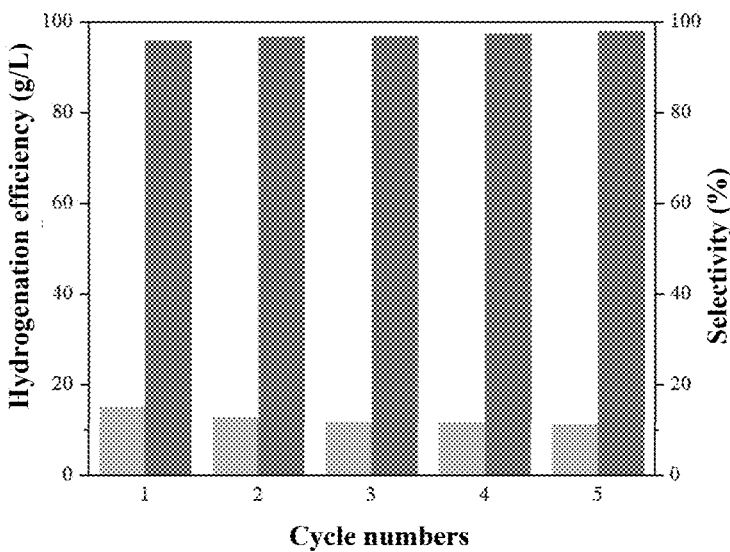
FIG. 6 shows the reusability of the $Pd^{\delta+}Mo_3S_3/Al_2O_3$ catalyst prepared in Embodiment 1 in selective hydrogenation reaction of anthraquinone.
Figure 7:
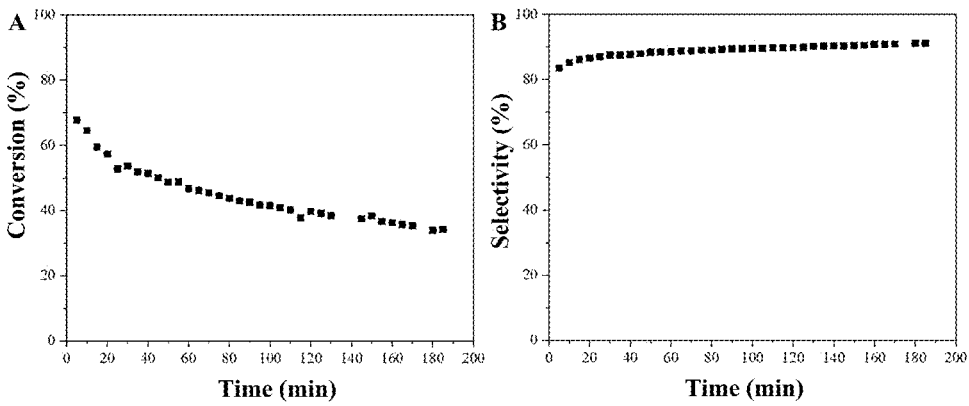
FIG. 7 shows the catalytic results of the $PtMo_3S_3/Al_2O_3$ catalyst prepared in Embodiment 2 in propane dehydrogenation, where A is the curve of propane conversion versus time, and B is the curve of propylene selectivity versus time.
Figure 8:
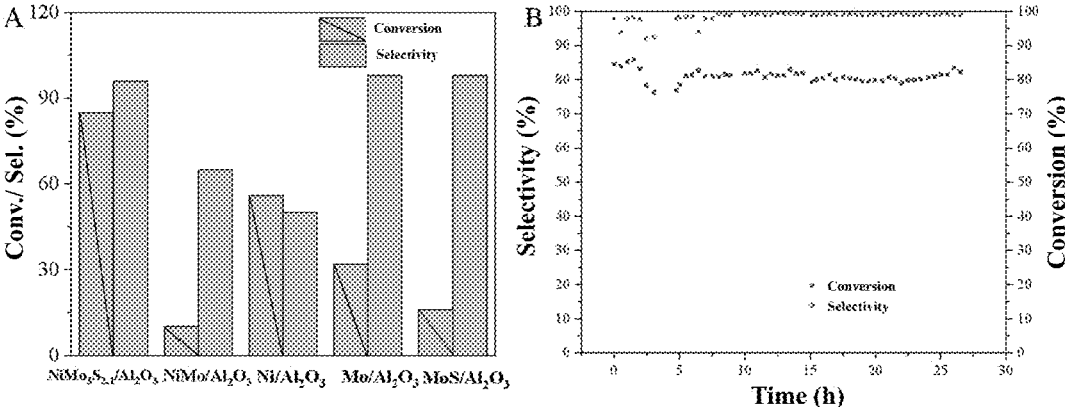
FIG. 8 shows the catalytic results of $NiMo_3S_{2.1}/Al_2O_3$ catalyst prepared in Embodiment 3 in the hydrodechlorination of dichloroethane, where A is the histogram of conversion and selectivity, and B is the reusability curve.

It can be seen from FIG. 5 that the hydrogenation efficiency of the catalyst reaches 15.7 g/L when the reaction time is 120 min. Compared with the 11.9 g/L in the Enhanced Catalytic Performance of Pd—Ga Bimetallic Catalysts for 2-ethylanthraquinone Hydrogenation. Appl Organometal Chem. 2019, 33, e5076, the hydrogenation efficiency is significantly improved. It can be seen from FIG. 6 that the hydrogenation efficiency of the catalyst remains at 11.2 g/L and the target product selectivity is 96% 2% after reusing for five times.

Embodiment 2

A. Stir and mix 10.0 mL soluble metallic $H_2PtCl_6$ solution with a concentration of 15.0 mmol/L and $[Mo_3S_4(H_2O)_9]Cl_4$ solution at a Pt/$Mo_3S_4$ molar ratio of 1:1 to obtain a solution containing heteronuclear Pt-based $[Mo_3PtS_4(H_2O)_{10}]Cl_4$ atomic cluster;

B. According to the theoretical loading of the metallic M being 2.00 wt. %, disperse 1.48 g $Al_2O_3$ support uniformly into the mixed solution obtained in step A, continuously stir at 60° C. and 300 rpm for 4 h until it becomes sticky, and dry it in a constant temperature drying oven at 60° C. for 24 h to obtain $[Mo_3PtS_4(H_2O)_{10}]Cl_4/Al_2O_3$ solid powder;

C. Add 1.5 g solid powder obtained in step B into 10 mL deionized water, add 0.0533 g $NaBH_4$ as a reducing agent, stir for 30 minutes, centrifuge and wash the obtained black suspension to neutral while washing away soluble sodium salts, and dry it at 60° C. in a constant temperature drying oven for 12 h to obtain $Mo_3PdS_4/Al_2O_3$;

D. Place the $Mo_3PdS_4/Al_2O_3$ obtained in step C into an atmosphere furnace, heat it to 570° C. at the rate of 10° C./min in 10% $H_2/N_2$ and treat it for 0.33 h to obtain the $Mo_3PtS_x/Al_2O_3$ catalyst; and the corresponding $Mo_3PtS_x/Al_2O_3$ catalyst (x=3) has $Pt_{iso}$-$V_s$ synergistic sites.

The catalyst is used in propane dehydrogenation:

Weigh 0.20 g catalyst and mix it with 1.80 g quartz sand with a particle size of 40-70 mesh thoroughly, and then load it into a quartz tube reactor with a diameter of 8 mm. The reaction feed gas is composed of 2.0% propane, 4% hydrogen and 94% nitrogen equilibrium gas, and the testing temperature is 580° C. The gas chromatography is used to analyze the composition and content of reactants and products. When the reactor reaches the specified temperature, records are made every 5 minutes. The results of propane conversion rate and selectivity of the catalyst at 580° C. are shown in Table 2.

TABLE 2

| Catalytic performance | | |
|---|---|---|
| | Embodiment 1 | |
| Sample | Selectivity (%) | Conversion rate (%) |
| Embodiment 2 | 90 | 68 |

The Pt—Sn catalyst in the literature ACS Catal. 2021, 11, 8, 4401-4410 is a commonly used catalyst for industrial propane dehydrogenation, with a selectivity of 92% and a conversion rate of 40% for propane dehydrogenation at 600° C. It can be seen from Table 2 that compared with the Pt—Sn catalyst reported in the literature, the $PtMo_3S_3/Al_2O_3$ catalyst prepared by the present invention has similar selectivity and more preferred activity at a lower temperature.

Embodiment 3

A. Stir and mix 6.7 mL soluble metallic $Ni(NO_3)_2\cdot6H_2O$ solution with a concentration of 0.19 mol/L and 5 mL $[Mo_3S_4(H_2O)_9]Cl_4$ solution with a concentration of 12.8 mmol/L to obtain a solution containing heteronuclear Ni-based $[Mo_3NiS_4(H_2O)_{10}]Cl_4$ atomic cluster;

B. According to the theoretical loading of metallic Ni being 2.5 wt. % of the catalyst, disperse 3.0 g $Al_2O_3$ support uniformly into 10.00 mL mixed solution obtained in step A, continuously stir at 60° C. and 400 rpm for 5 h until it becomes sticky, and dry it in a constant temperature drying oven at 60° C. for 12 h to obtain $[Mo_3NiS_4(H_2O)_{10}]Cl_4/Al_2O_3$ solid powder;

C. Add 1.5 g solid powder obtained in step B into 10 mL deionized water, add 0.0533 g $NaBH_4$ as a reducing agent, stir for 30 minutes, centrifuge and wash the obtained black suspension to neutral while washing away soluble sodium salts, and dry it at 60° C. in a constant temperature drying oven for 12 h to obtain $Mo_3NiS_4/Al_2O_3$;

D. Place the $Mo_3NiS_4/Al_2O_3$ obtained in step C into an atmosphere furnace, heat it to 450° C. at the rate of 10° C./min in 10 vol. % $H_2/N_2$ and conduct heat treatment for 3 h to obtain the $Mo_3NiS_x/Al_2O_3$ catalyst; and the corresponding $Mo_3NiS_x/Al_2O_3$ catalyst (x=2.1) has $Ni_{iso}$—$V_s$ synergistic sites.

The catalyst is used in the 1,2-dichloroethane hydrodechlorination:

Weigh 0.30 g catalyst and mix it with 1.40 g quartz sand with a particle size of 40~70 mesh thoroughly, and then load it into a quartz tube reactor with a diameter of 7 mm. The reaction feed gas is composed of 92% 1,2-dichloroethane mixture and 8% hydrogen/nitrogen mixture, and the testing temperature is 300° C. The gas chromatography is used to analyze the composition and content of reactants and products. When the reactor reaches the specified temperature, records are made every 10 minutes. The results of 1,2-dichloroethane conversion rate and selectivity of the catalyst at 300° C. are shown in Table 3.

TABLE 3

| Catalytic performance | | |
|---|---|---|
| | Embodiment 1 | |
| Sample | Selectivity (%) | Conversion rate (%) |
| Embodiment 3 | 96 | 85 |

According to the literature Chem. Commun. 2020, 56, 6985, the selectivity of 17Ni—PC@SBA-15 catalyst for the hydrodechlorination of 1,2-dichloroethane at 300° C. is 90%, and the conversion is 65.5%. It can be seen from Table 3 that compared with the 17Ni—PC@SBA-15 catalyst reported in the literature, the selectivity and activity of the $NiMo_3S_{2.1}/Al_2O_3$ catalyst prepared by the present invention are higher than those of the above-mentioned 17Ni—PC@SBA-15 catalyst at the same temperature.

Embodiment 4

A. Stir and mix 5.64 mL soluble metallic $Na_2PdCl_4$ solution with a concentration of 50 mmol/L and 5 mL $[Re_3S_4(H_2O)_9]Cl$ solution with a concentration of 12.8 mmol/L to obtain a solution containing heteronuclear Pd-based $[Re_3PdS_4(H_2O)_9]Cl$ atomic cluster;

B. Calcine pseudo-boehmite at 960° C. to obtain $Al_2O_3$ support with rich pore structure. Disperse 1.5 g $Al_2O_3$ support into 10.64 mL mixed solution obtained in step A at room temperature, with the loaded active metal Pd being 0.4 wt. %. Stir the mixture continuously for 4 h at 60° C. and 300 rpm until it becomes sticky, and dry it in a constant temperature drying oven at 60° C. for 12 h to obtain $[Re_3PdS_4(H_2O)_9]Cl/Al_2O_3$ solid powder.

C. Add 1.5 g solid powder obtained in step B into 10 mL deionized water, add 0.0533 g $NaBH_4$ as a reducing agent, stir for 30 minutes, centrifuge and wash the obtained black suspension to neutral while washing away soluble sodium salts, and have it dried at 60° C. in a constant temperature drying oven for 12 h to obtain $Re_3PdS_4/Al_2O_3$;

D. Place the $Re_3PdS_4/Al_2O_3$ obtained in step C into an atmosphere furnace, heat it to 450° C. at the rate of 10° C./min in air and calcine it for 4 h to obtain the $Re_3PdS_x/Al_2O_3$ catalyst; and the corresponding $Re_3PdS_x/Al_2O_3$ catalyst (x=3) has $Pd_{iso}$—$V_s$ synergistic sites.

Embodiment 5

A. Stir and mix 14.10 mL soluble metallic $Na_2PdCl_4$ salt solution with a concentration of 50 mmol/L and 5 ml $[Mo_3S_4(H_2O)_9]Cl_4$ solution with a concentration of 12.8 mmol/L to obtain a solution containing heteronuclear Pd-based $[Mo_3PdS_4(H_2O)_{10}]$ atomic cluster;

B. Calcine pseudo-boehmite at 960° C. to obtain $Al_2O_3$ support with rich pore structure. Disperse 1.5 g $Al_2O_3$ support into 12.05 mL mixed solution obtained in step A at room temperature, in which the supported active metal Pd is 1.0 wt. %. Stir the mixture continuously for 4 h at 40° C. and 300 rpm until it becomes sticky, and dry it in a constant temperature drying oven at 40° C. for 12 h to obtain $[Mo_3PdS_4(H_2O)_{10}]Cl_4/Al_2O_3$ solid powder.

C. Add 1.5 g solid powder obtained in step B into 10 mL deionized water, add 0.0666 g $NaBH_4$ as a reducing agent, stir for 30 minutes, centrifuge and wash the obtained black suspension to neutral while washing away soluble sodium salts, and dry it at 60° C. in a constant temperature drying oven for 12 h to obtain $Mo_3PdS_4/Al_2O_3$;

D. Place the $Mo_3PdS_4/Al_2O_3$ obtained in step C into an atmosphere furnace, heat it to 450° C. at the rate of 10° C./min in air and calcine it for 4 h to obtain the $Mo_3PdS_x/Al_2O_3$ catalyst; and the corresponding $Mo_3PdS_x/Al_2O_3$ catalyst (x=3) has $Pd_{iso}$—$V_s$ synergistic sites.

Embodiment 6

A. Stir and mix 6.7 mL soluble metallic $CuCl_2·2H_2O$ solution with a concentration of 0.19 mol/L and 5 mL $[Mo_3S_4(H_2O)_9]Cl_4$ solution with a concentration of 12.8 mmol/L to obtain a solution containing heteronuclear Cu-based $[Mo_3CuS_4(H_2O)_{10}]Cl$ atomic cluster;

B. According to the theoretical loading of metallic Cu being 2.50 wt. %, disperse 3.0 g $Al_2O_3$ support uniformly into 10.00 mL mixed solution obtained in step A, continuously stir at 60° C. and 400 rpm for 5 h until it becomes sticky, and dry it in a constant temperature drying oven at 60° C. for 12 h to obtain $[Mo_3CuS_4(H_2O)_{10}]Cl_4/Al_2O_3$ solid powder;

C. Add 1.5 g solid powder obtained in step B into 10 mL deionized water, add 0.0533 g $NaBH_4$ as a reducing agent, stir for 30 minutes, centrifuge and wash the obtained black suspension to neutral while washing away soluble sodium salts, and dry it at 60° C. in a constant temperature drying oven for 12 h to obtain $Mo_3CuS_4/Al_2O_3$;

D. Place the $Mo_3CuS_4/Al_2O_3$ obtained in step C into an atmosphere furnace, heat it to 400° C. at the rate of 5° C./min in 10 vol. % $H_2/N_2$ and conduct heat treatment for 3 h to obtain the $Mo_3CuS_x/Al_2O_3$ catalyst; and the corresponding $Mo_3CuS_x/Al_2O_3$ catalyst (x=2.5) has $Cu_{iso}$—$V_s$ synergistic sites.

The invention claimed is:

1. A preparation method of a supported metal catalyst with synergistic sites, characterized in that the preparation method comprises the following steps:

A. Mix a soluble metal M salt solution uniformly with a solution of [X3S4(H2O)y]Clz cluster compound to obtain a [X3MS4(H2O)y+1]z+ solution;

B. Disperse Al2O3 support uniformly into the solution obtained in step A, stir at the temperature of 25-60° C. and the rotation speed of 200~500 rpm for 2-6 h until it becomes sticky, and dry it in a constant temperature drying oven at 40~80° C. for 8-24 h to obtain [X3MS4(H2O)y+1]z+/Al2O3 solid powder;

C. Add 1.5 g solid powder obtained in step B into 5-30 mL of deionized water, add excessive soluble reducing agent to reduce M2+/M3+ to metal M, wherein the molar ratio of the reducing agent to the M salt is 3:1~7:1, stir for 18~60 min to obtain black suspension, centrifugally wash it to neutrality, and dry it in a constant temperature drying oven at 60° C. for 8-16 h to obtain X3MS4/Al2O3;

D. Place the X3MS4/Al2O3 obtained in step C into an atmosphere furnace, and heat it to 300~600° C. at a rate of 5-20° C./min for 0.25-6 h of treatment to obtain X3MSx/Al2O3 catalyst (0<x<4);

The corresponding treatment atmosphere is one of air, 10 vol. % O2/N2, 5-40 vol. % H2/N2 or 5-40 vol. % CO/N2; The corresponding X3MSx/Al2O3 catalyst possesses Miso-Vs synergistic sites;

Wherein, the corresponding [X3S4(H2O)y]Clz in step A is a trinuclear transition metal-sulfur cluster compound with an unsaturated cubane structure, wherein X is one of Mo, W, Re and Ir; y=9; when X is Re (+3), z=1; when X is one of W, Mo and Ir(+4), z=4.

2. A preparation method of a supported catalyst with synergistic sites according to claim 1, characterized in that the corresponding soluble metal M salt in step A is one of Na2PdCl4, Pd(NO3)2, Pd(C5H7O2)2, H2PtCl6, Pt(NO3)2, CoCl2, Ni(NO3)2·6H2O, NiCl2, RuCl3, Ga(NO3)3, Fe(NO3)3·9H2O, CuCl2·2H2O, Cu(NO3)2 and AgNO3.

3. A preparation method of a supported catalyst with synergistic sites according to claim 1, characterized in that the molar ratio of M to X3 in step A is 4~25/l, and the concentration of the M salt is 0.0035~0.0171 mol/L.

4. A preparation method of a supported catalyst with synergistic sites according to claim 1, characterized in that the theoretical loading of the soluble metal M salt in step B is 0.03~5.00 wt. % of the catalyst; the corresponding Al2O3 support possesses rich pore structure while the crystalline phases is γ or δ, the specific surface area is 70~190 m2/g, the pore volume is 0.3~1.3 cm3/g, and the pore size is 15~30 nm; the soluble reducing agent in step C is one of NaBH4, LiBH4, ascorbic acid or oxalic acid.

* * * * *